(12) United States Patent
Shakhnovich et al.

(10) Patent No.: US 11,427,557 B2
(45) Date of Patent: Aug. 30, 2022

(54) SYNERGISTS FOR QUINACRIDONE MAGENTA PIGMENTS

(71) Applicant: Cabot Corporation, Boston, MA (US)

(72) Inventors: Alexander I. Shakhnovich, Arlington, MA (US); Heather E. Clarke, Lancaster, MA (US)

(73) Assignee: Cabot Corporation, Boston, MA (US)

( * ) Notice: Subject to any disclaimer, the term of this patent is extended or adjusted under 35 U.S.C. 154(b) by 274 days.

(21) Appl. No.: 16/887,135

(22) Filed: May 29, 2020

(65) Prior Publication Data

US 2020/0377470 A1    Dec. 3, 2020

Related U.S. Application Data

(60) Provisional application No. 62/854,524, filed on May 30, 2019.

(51) Int. Cl.
    *C07D 401/04*      (2006.01)
    *C07D 401/14*      (2006.01)
    *C09D 11/322*     (2014.01)

(52) U.S. Cl.
    CPC ......... *C07D 401/04* (2013.01); *C07D 401/14* (2013.01); *C09D 11/322* (2013.01)

(58) Field of Classification Search
    CPC .............................. C07D 401/04; C07D 401/14
    USPC ...................................................... 106/31.77
    See application file for complete search history.

(56) References Cited

U.S. PATENT DOCUMENTS

| | | | |
|---|---|---|---|
| 5,750,323 A | 5/1998 | Scaringe et al. | |
| 7,166,158 B2 | 1/2007 | Mitina et al. | |
| 9,612,263 B2 * | 4/2017 | Murata | G01R 19/0092 |
| 2016/0326391 A1 | 11/2016 | Doumaux et al. | |

FOREIGN PATENT DOCUMENTS

| | | |
|---|---|---|
| EP | 1790695 A1 | 5/2007 |
| WO | WO 2005/049735 A2 | 6/2005 |
| WO | WO 2006/117303 A2 | 11/2006 |

\* cited by examiner

Primary Examiner — Niloofar Rahmani

(57) ABSTRACT

Disclosed herein are compositions (e.g., pigment dispersions or ink compositions such as inkjet ink compositions) comprising at least one quinacridone magenta pigment and at least one synergist selected from compounds (A) and (B) having the following structures, wherein each n is an integer independently ranging from 1 to 4, and $R_1$-$R_3$ are each independently selected from H, $CH_3$, Cl, and F, (A)

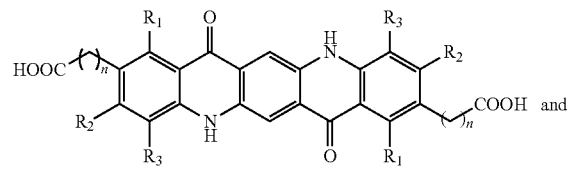

and (B)

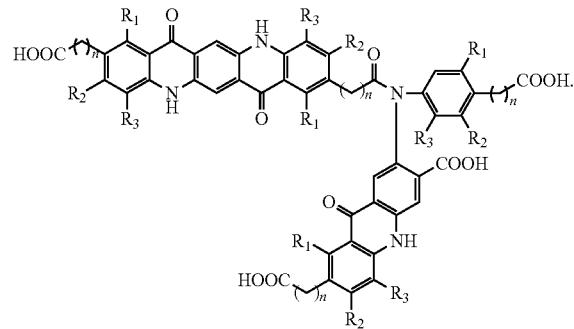

18 Claims, No Drawings

SYNERGISTS FOR QUINACRIDONE MAGENTA PIGMENTS

FIELD OF THE INVENTION

Disclosed herein are compositions comprising quinacridone magenta pigments and synergists having a structure based on quinacridones. Such compositions can be useful in pigment dispersions and ink (e.g., inkjet ink) applications.

BACKGROUND

In general, pigments are not readily dispersible in aqueous liquid vehicles, which creates challenges for formulating pigment-based inks. To improve dispersibility, various developments have been undertaken, including the use of dispersing aids or dispersants, which are typically surfactants and water-soluble polymers. Alternatively, the pigment can be modified to include ionic compounds, rendering the pigment self-dispersible. These strategies, however, may not be optimal for certain formulation types. Accordingly, there remains a need to develop methods for dispersing pigments in aqueous vehicles.

SUMMARY

Disclosed herein are compositions comprising at least one quinacridone magenta pigment and at least one synergist selected from compounds (A) and (B) having the following structures:

(A)

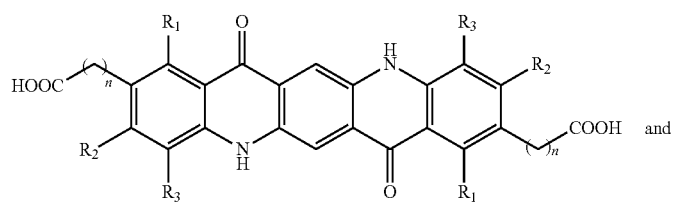

and (B)

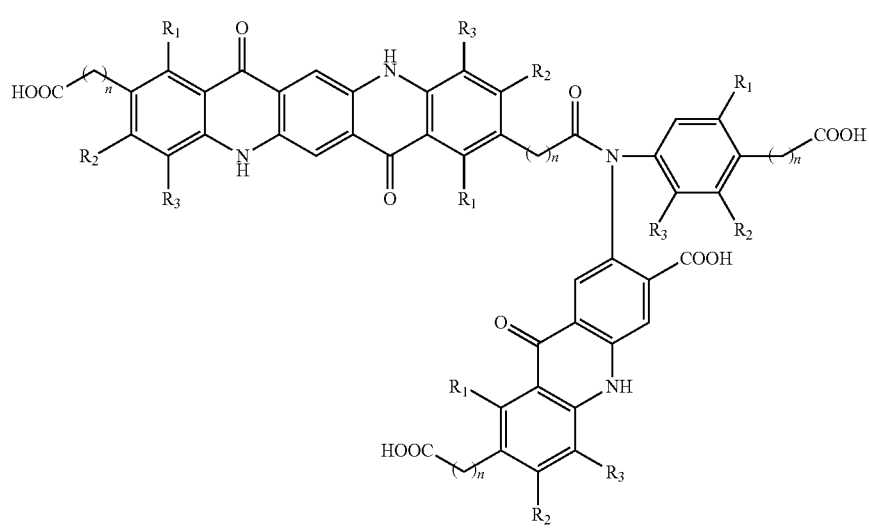

wherein each n is an integer independently ranging from 1 to 4, and $R_1$-$R_3$ are each independently selected from H, $CH_3$, Cl, and F.

Also disclosed are pigment dispersions and ink compositions (e.g., inkjet ink compositions) comprising such pigments and synergists.

DETAILED DESCRIPTION

Disclosed herein are compositions comprising at least one quinacridone pigment. Quinacridones are a primary class of magenta colorants for ink (e.g., inkjet ink) applications and are useful due to their permanence and clean color. Quinacridones are flat pentacyclic molecules having the following base structure:

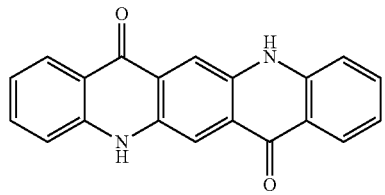 [SMILES: O=c1c2ccccc2[nH]c2cc3c(=O)c4ccccc4[nH]c3cc12]

Different types of quinacridones can be obtained by substituting the hydrogen atoms of the aryl groups, for example, with groups such as alkyl groups (e.g., methyl) or Cl atoms. The present magenta pigments are based on a quinacridone structure in which exemplary pigments include Pigment Violet 19, Pigment Red 122, Pigment Red 192, Pigment Red 202, Pigment Red 207, Pigment Red 209, and Pigment Red 282.

As is typical for pigments, quinacridone are largely insoluble/non-dispersible in aqueous media. It has been discovered that the incorporation of at least one quinacridone dispersant having at least one ionic functional group can impart dispersibility to the quinacridone pigment in an aqueous pigment dispersion or ink (e.g., inkjet ink) composition. In one embodiment, the dispersant is a synergist, e.g., a compound that is structurally similar to the pigment. By structurally similar, it is meant that the synergist contains an identical structural section and a distinct structural section. In one embodiment, the identical structural section comprises at least 50% of the total molecular weight of the pigment, e.g., at least 60%, at least 70%, at least 80% or at least 90% of the total molecular weight of the pigment. In one embodiment, the synergist is a derivative of the magenta pigment, e.g., a derivative of the quinacridone. Thus, the synergist is a material separate from the pigment that is capable of providing a stable dispersion of the pigment in a liquid vehicle. The synergist is therefore not a material produced during the preparation of the pigment using, for example, known mixed coupling techniques.

Without wishing to be bound by any theory, the structural similarity between the pigment and synergist results in the synergist potentially having a high affinity for the pigment. A high affinity in turn can aid in the adsorption of the synergist to the pigment surface. In one embodiment, this high affinity can take the form of Van der Waals interactions (e.g., dipole-dipole interactions). In one embodiment, the synergist further comprises at least one ionic group that allows additional interactions between the pigment and synergist, including one or more of ionic interactions/bonding, hydrogen bonding, and acid/base interactions/reactions. In one embodiment, both the pigment and synergist have at least one ionic group, thereby providing interactions as described herein (e.g., Van der Waals interactions, ionic interactions/bonding, acid/base interactions/bonding, and hydrogen bonding). Moreover, adsorption of a synergist molecule on a face of pigment crystals can creates a dislocation, which potentially prevents further crystal growth along this face, thereby providing a handle to control and/or maintain the size and distribution of pigment particles.

The synergist can also have one or more functional groups different from those of the pigment, and such functional groups can be ionic or ionizable. In one embodiment, ionic group(s) of the at least one synergist provide hydrophilic properties that renders the synergist soluble or dispersible in a liquid vehicle, e.g., an aqueous solution. When the synergist is adsorbed to the quinacridone pigment, this adsorption can occur preferentially due to its similar structure. The synergist in effect can provide charged groups to the pigment surface to also render the pigment dispersible in a liquid vehicle (e.g., an aqueous solution).

Quinacridone compounds having carboxy groups ($-CO_2-$) directly bonded to the quinacridone ring system are known. While carboxy groups can provide the quinacridone with suitable hydrophilic properties to cause the compound to be soluble/dispersible in aqueous media, without wishing to be bound by any theory, the close proximity of the carboxy groups to the quinacridone ring may interfere with the adsorption of the synergist's quinacridone structure to that of the quinacridone pigment, which may reduce the capability of the synergist to render the pigment dispersible or otherwise prevent the synergist from imparting dispersibility properties to the pigment. As synergists are additives, the use of synergists can simplify the ink formulation process by avoiding a purification step, which may be required in other dispersion techniques, such as with dispersant additives.

In one embodiment, the at least one synergist has the following structure (A):

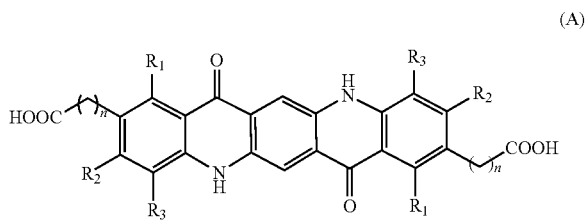

wherein each n is an integer independently ranging from 1 to 4, and $R_1$-$R_3$ are each independently selected from H, $CH_3$, Cl, and F. With n ranging from 1 to 4, the resulting carboxy group is bonded to the quinacridone via methylene, ethylene, propylene, or butylene, respectively. In one embodiment, n is selected from 1 or 2. In another embodiment, n is 1. In one embodiment, $R_1$-$R_3$ are independently selected from H, $CH_3$, and Cl, e.g., from H and $CH_3$. In another embodiment, $R_1$-$R_3$ are each H.

The presently claimed synergists can be made from methods well known in the art, e.g., by reacting dialkyl succinylsuccinate (e.g., dimethyl succinylsuccinate) with an aniline having the desired carboxy-terminated substituent(s), e.g., p-aminophenylacetic acid, p-aminophenylpropanoic acid, p-aminophenylbutanoic acid, or p-aminophenylpentanoic acid.

In one embodiment, the reaction between dialkyl succinylsuccinate and the p-aniline-carboxy terminated compound can further result in a dimeric compound having the structure (B):

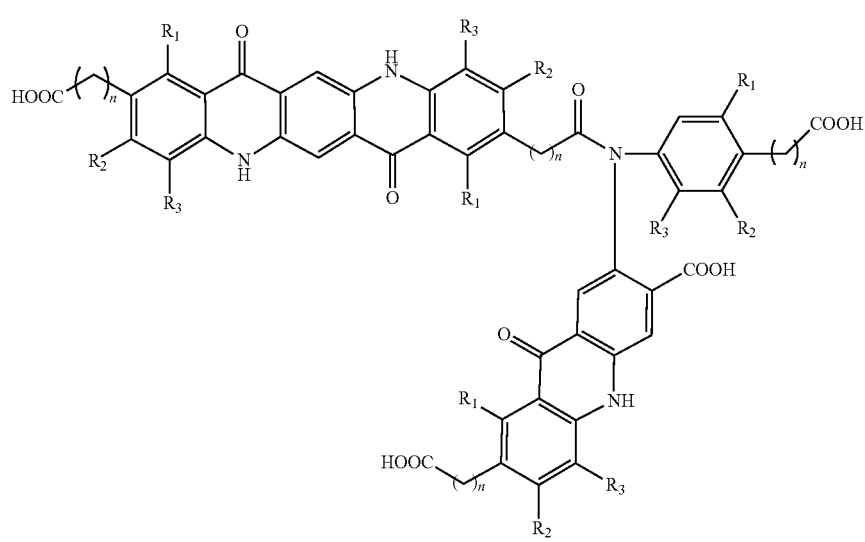

(B)

wherein n and $R_1$-$R_3$ are as defined previously.

In one embodiment, the composition comprising the at least one quinacridone magenta pigment further comprises at least one synergist selected from compounds having the structure (A) only, from structure (B) only, or a mixture of both structure (A) and structure (B). In one embodiment, the composition comprises a mixture of synergists having structure (A) and (B). The mixture of synergists (A) and (B) can be present in a ratio (A):(B) ranging from 1:10 to 10:1, e.g., from 1:5 to 5:1, or from 1:2 to 2:1. In one embodiment, the composition is a pigment dispersion or ink (e.g., inkjet ink) composition comprising at least one synergist selected from compounds having the structure (A) and/or (B). Whether one of synergists (A) or (B) or both are present in the composition, the at least one synergist is present in the composition (e.g., total amount of synergist) in an amount ranging from 3% to 10% by weight relative to the weight of the at least one quinacridone magenta pigment. For example, the at least one synergist is present in the composition in an amount ranging from 3% to 9%, from 4% to 10%, from 4% to 9%, from 5% to 10%, or from 5% to 9% by weight relative to the weight of the at least one quinacridone magenta pigment.

In one embodiment, the at least one synergist in the composition is a mixture of more than one compound having the structure (A), e.g., with different n values and/or independently different $R_1$-$R_3$ substituents. In one embodiment, the at least one synergist in the composition is a mixture of more than one compound having the structure (B), e.g., with different n values and/or independently different $R_1$-$R_3$ substituents. In yet another embodiment, the at least one synergist in the composition is a mixture of one or more compounds having the structure (A) and one or more compounds having the structure (B), e.g., with different n values and/or independently different $R_1$-$R_3$ substituents Pigments are solid materials generally in the form of a particulate solid. The particulate solid can be a powder, a dispersion, or a pressed cake. Such particle sizes can be achieved by one or more conventional size reduction, comminution, and/or classification techniques, such as ball milling, media milling, jet milling, sonication, fluid impingement, and centrifugation to remove undesired large particles. Median particle size can be determined by dynamic light scattering techniques with equipment produced by companies such as Microtrac, Inc., and Malvern Panalytical, Ltd., as examples. In one embodiment, the pigment has a median particle size ranging from ranging from 100 nm to 300 nm, e.g., from 100 nm to 250 nm, from 100 nm to 225 nm, from 100 nm to 200 nm, from 100 nm to 180 nm, from 120 nm to 250 nm, from 120 nm to 225 nm, from 120 nm to 200 nm, from 120 nm to 180 nm, from 150 nm to 250 nm, from 150 nm to 225 nm, from 150 nm to 200 nm, or from 150 nm to 180 nm. Dispersions comprising the pigment can be purified by ultrafiltration, diafiltration, ion exchange, centrifugation, or a combination of one or more such methods.

It has been discovered that the claimed synergist enhances the stability of the quinacridone pigment. Stability can be gauged by median particle size of the pigment in a dispersion or an ink. In one embodiment, the median particle size of the pigment in the pigment dispersion or ink containing the claimed synergist does not significantly increase in size over a certain time period, e.g., at least 7 days, or at least two weeks, or at least 6 weeks, either at room temperature or at 60° C. In one embodiment, the median particle size does not increase by more 30% relative to its initial median particle size. For example, the median particle size does not increase by more than 25%, does not increase by more than 20%, does not increase by more than 15%, does not increase by more than 10%, or does not increase by more than 10% relative to its initial median particle size. When the median particle size of a pigment increases by more than 30% relative to its initial median particle size (or other percentages as described herein), typically this occurs as a result of agglomeration, which can cause the pigment to settle and/or gel.

Without wishing to be bound by any theory, the quinacridone synergist having the structure (A) or (B) features carboxy groups that are separated from the quinacridone ring system by at least one methylene group (e.g., an ethylene, a propylene, or a butylene group). This separation of the carboxy group from the quinacridone ring system may allow for better adsorption of the synergist ring system to the corresponding pigment ring system.

In one embodiment, the composition comprises a liquid vehicle. In one embodiment, the liquid vehicle is aqueous. For example, an aqueous vehicle can be an aqueous solution, e.g., comprises at least 40% water, e.g., at least 45% water or at least 50% water. In one embodiment, the composition is a pigment dispersion, e.g., an aqueous pigment dispersion. In another embodiment, the composition is an ink (e.g., inkjet ink) composition, e.g., an aqueous ink (e.g., inkjet ink) composition.

In one embodiment, the composition is an aqueous pigment dispersion comprising the quinacridone magenta pigment in an amount ranging from 1% to 40% by weight relative to the total weight of the pigment dispersion, e.g., from 1% to 30%, from 1% to 20%, from 1% to 10%, from 3% to 40%, from 3% to 30%, from 3% to 20%, from 3% to 10%, from 5% to 40%, from 5% to 30%, from 5% to 20%, or from 5% to 10% by weight relative to the total weight of the pigment dispersion.

In one embodiment, the composition is an aqueous ink (e.g., inkjet ink) composition. In one embodiment, the composition comprises the magenta quinacridone pigment in an amount ranging from 1% to 15% by weight, e.g., from 1% to 10% by weight, relative to the total weight of the composition, e.g., an amount ranging from 2% to 15%, from 2% to 10% by weight, from 3% to 15%, from 3% to 10% by, from 1% to 7%, from 2% to 7%, or from 3% to 7% by weight, relative to the total weight of the composition.

In one embodiment, the composition, e.g., aqueous pigment dispersion or aqueous ink (e.g., inkjet ink) composition further comprises at least one organic solvent present in an amount ranging from 1% to 50% relative to the total weight of the inkjet ink composition. The at least one organic solvent can be present in the composition in addition to at least 40% water (or at least 45% water or at least 50% water). In one embodiment, the organic solvent is soluble or miscible in water. In another embodiment, the organic solvent is chemically stable to aqueous hydrolysis conditions (e.g., reaction with water under heat aging conditions, including, for example, the hydrolysis of esters and lactones). In one embodiment, the organic solvent has a dielectric constant below that of water, such as a dielectric constant ranging from about 10 to about 78 at 20° C. Examples of suitable organic solvents include alcohols and polyols (glycols, glycerols, etc.), amides, ketones or ketoalcohols, ethers, ureas or urea derivatives, hydroxyamide derivatives, saccharides, sulfoxide derivatives, and sulfone derivatives. The at least one organic solvent can comprise mixtures of organic solvents.

Humectants and water-soluble organic compounds other than the at least one organic solvent may also be added to the inkjet ink composition of the present invention, e.g., for the purpose of preventing clogging of the nozzle as well as for providing paper penetration (penetrants), improved drying (drying accelerators), and anti-cockling properties. In one embodiment, the humectant and/or water-soluble compound is present in an amount ranging from 0.1% to 50%, e.g., an amount ranging from 1% to 50%, from 0.1% to 30%, from 1% to 30%, from 0.1% to 10%, or from 1% to 10%.

In one embodiment, an ink composition (e.g., an inkjet ink composition) comprises at least one surfactant, e.g., when the pigment is not self-dispersible. The at least one surfactant can enhance the colloidal stability of the composition or change the interaction of the ink with either the printing substrate, such as printing paper, or with the ink printhead. Various anionic, cationic and nonionic dispersing agents can be used in conjunction with the ink composition of the present invention, and these may be used neat or as a water solution. In one embodiment, the surfactant is present in an amount ranging from 0.05% to 5%, e.g., an amount ranging from 0.1% to 5%, or from 0.5% to 2%, by weight relative to the total weight of the inkjet ink composition.

In one embodiment, the ink (e.g., inkjet ink) composition has a viscosity ranging from 1-25 cP. It is understood that viscosity can be adjusted by a variety of methods. In one embodiment, polymeric binders can be used in conjunction with the inkjet ink composition disclosed herein to adjust the viscosity of the composition and/or provide other desirable properties, such as durability (e.g., at least one durability polymer). Such polymeric binders can be present in the composition in an amount ranging from 0.1% to 20% by weight relative to the total weight of the composition, e.g., an amount ranging from 0.1% to 10%, from 0.1% to 5%, from 0.2% to 20%, from 0.2% to 10%, from 0.2% to 5%, from 0.5% to 20%, from 0.5% to 10%, or from 0.5% to 5% by weight relative to the total weight of the composition.

In one embodiment, the ink (e.g., inkjet ink) composition can further comprise one or more suitable additives to impart a number of desired properties while maintaining the stability of the compositions. Other additives are well known in the art and include humectants, biocides and fungicides, pH control agents, drying accelerators, penetrants, and the like. The amount of a particular additive will vary depending on a variety of factors but are generally present in an amount ranging between 0.01% and 40% based on the weight of the ink composition. In one embodiment, the at least one additive is present in an amount ranging from 0.05% to 5%, e.g., an amount ranging from 0.1% to 5%, or an amount ranging from 0.5% to 2%, by weight relative to the total weight of the inkjet ink composition

EXAMPLES

Reaction products were identified by HPLC-M/S (Agilent 1100 connected to a Thermo LTQ XL with Electrospray ionization; column: Zorbax Extend C18, 4.6×150 mm, 5 um), from Agilent Technologies, Inc. Particle sizes were measured by using a Nanotrac™ 252 particle size analyzer produced by Microtrac, Inc.

These Examples describe the preparation of quinacridone synergists according to the claimed invention: 2,9-bis(carboxymethyl)quinacridone (V) and its corresponding dimer (VI). Also disclosed is the preparation of a comparative quinacridone compound, 2,9-dicarboxyquinacridone (IV).

Preparation of 2,9-dicarboxyquinacridone (IV) (Comparative)

The preparation of a comparative quinacridone (IV) is illustrated in Scheme (1).

Scheme 1

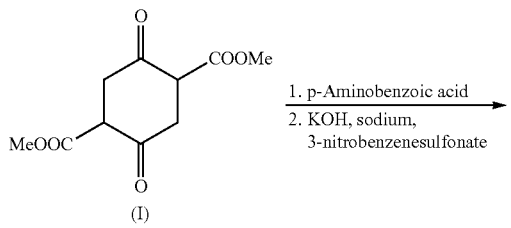

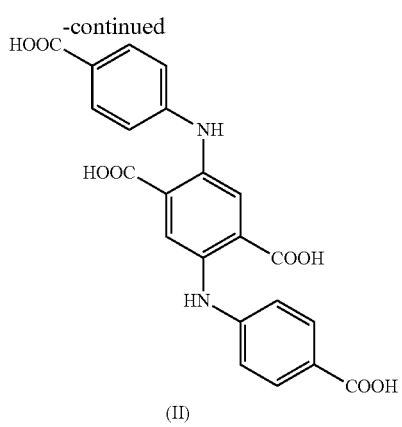

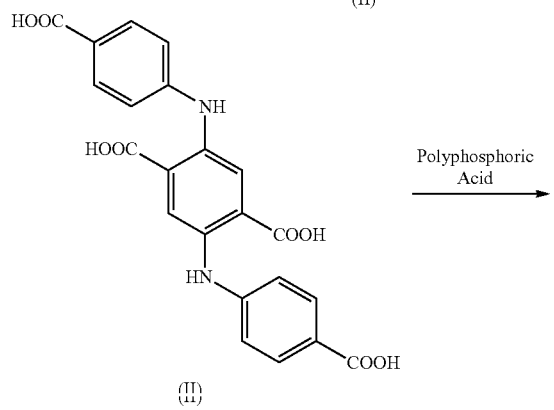

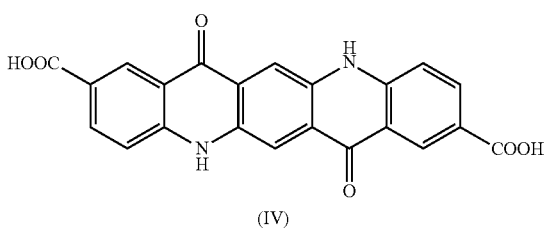

A mixture of dimethyl succinylsuccinate (I) (60 g), p-aminobenzoic acid (82.8 g), HCl (4 ml, 37%), and ethanol (800 ml) was refluxed under nitrogen for 5 hours and cooled to 65° C. Sodium 3-nitrobenzenesulfonatesulfonate (69.2 g) was then added, followed by the addition of 200 g of a 45% KOH solution. This mixture was refluxed for another 4 hours. The resulting dispersion was diluted with 600 ml of water and filtered. The filtrate was acidified with 37% hydrochloric acid, filtered at 45° C., and washed with water, resulting in a magenta powder (II) (yield=130 g). Prior to cyclization, the powder was dried and ground. Purity by HPLC was 98.2%.

Polyphosphoric acid (85% $P_2O_5$, 500 g, Aldrich) was heated to 90° C. Under intensive stirring, 50 g of ground powder (II) was added. The temperature was raised to 135° C. and the reaction mixture was stirred for 5 hours and then cooled to 60-70° C. The mixture was poured into 2 liters of water and stirred for 1 hour. The resulting precipitated quinacridone (IV) was filtered under vacuum, washed with 3 liters of deionized water, and dried in a vacuum oven at 60° C. overnight. The yield of the resulting dark red powder was 41.2 g; purity by HPLC was 94.3%.

Preparation of 2,9-bis(carboxymethyl)quinacridone (V) and its Dimer (VI)

Scheme (2) shows the preparation of a quinacridone synergist according to the claimed invention and its corresponding dimer.

Scheme 2

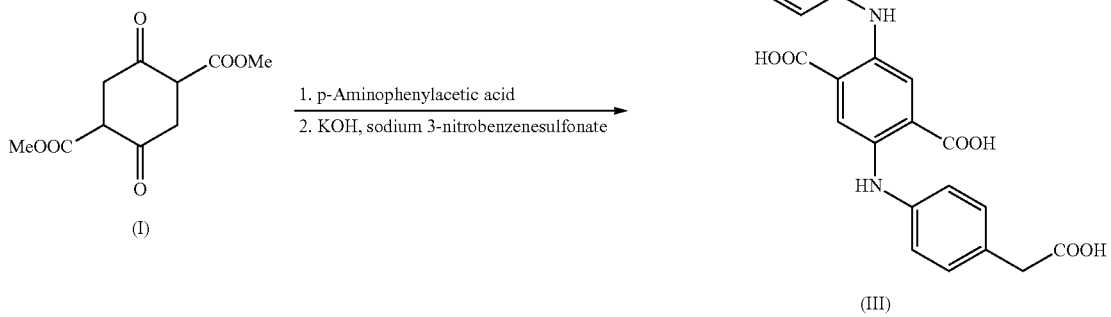

-continued

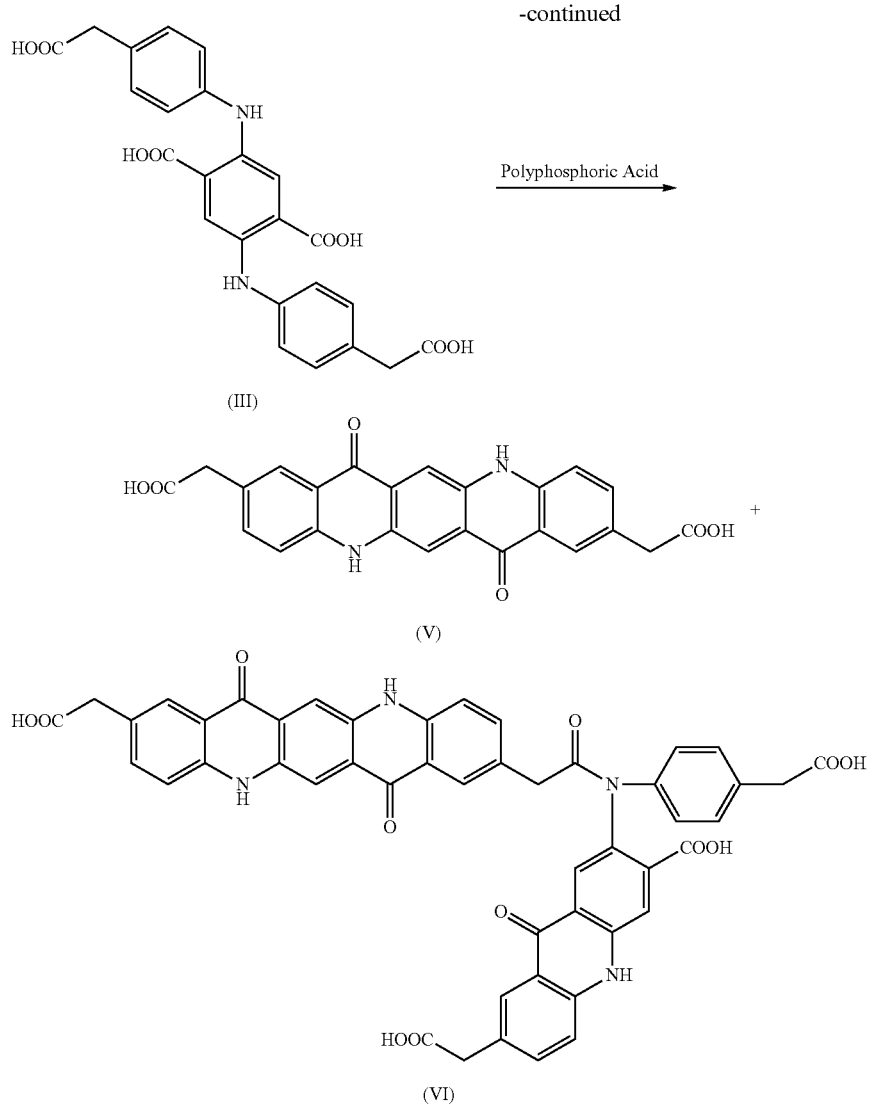

A mixture of dimethyl succinylsuccinate (I) (30 g), p-aminophenylacetic acid (40.9 g), HCl (2 ml, 37%), and ethanol (500 ml) was refluxed under nitrogen for 5 hours and cooled to 65° C. Sodium 3-nitrobenzenesulfonatesulfonate (34.6 g) was added, followed by the addition of 80 g of 45% KOH solution. This mixture was refluxed for another 4 hours. The resulting dispersion was diluted with 600 ml of water and filtered. The filtrate was acidified with 37% hydrochloric acid, filtered at 45° C., and washed with water, resulting in a magenta powder (yield=51.2 g). Prior to cyclization, the powder was dried and ground. Purity by HPLC was 99%.

Polyphosphoric acid (85% $P_2O_5$, 500 g, Aldrich) was heated to 90° C. Under intensive stirring, 50 g of ground powder (III) was added. The temperature was raised to 140° C. and the reaction mixture was stirred for 4 hours and then cooled to 60-70° C. The mixture was poured into 2 liters of water and stirred for 1 hour. The resulting precipitated mixture of quinacridone (V) and its dimer (VI) was filtered under vacuum, washed with 3 liters of deionized water, and dried in a vacuum oven at 60° C. overnight. The yield of the resulting dark red powder was 42 g; purity of the mixture by HPLC was 90.6%. According to HPLC, the ratio of compound (V) to compound (VI) was 1.73.

Preparation of Pigment Dispersions

Comparative ("C1") and Example 1 dispersion ("Ex. 1"): In a stainless steel vessel, dry Pigment Red 122 (75 g, Ink Jet Magenta E 02, Clariant), 5.25 g of the synergist mixture (V)+(VI) was combined with 400 g water. Sodium hydroxide solution (27 ml, 1N) was added and the mixture was homogenized with an overhead rotor-stator high shear mixer (Silverson L4RT-A) for 1 hour at 5,000 rpm. The mixture was then sonicated for 2 hours at 180 watt power (Misonix sonicator). The obtained dispersions were centrifuged at 2,500 g to remove coarse particles. A dispersion containing comparative quinacridone (IV) was prepared in the same manner.

Example 2 dispersion ("Ex. 2"): In a stainless steel vessel, dry Pigment Red 122 (600 g, Ink Jet Magenta E 02, Clariant) and 36 g of synergist (V)+(VI) mixture were combined with 400 g water and 7 g of sodium carbonate. The mixture was homogenized with an overhead rotor-stator high shear mixer (Silverson L4RT-A) for 10 minutes at 5,000 rpm. The mixture was then milled with 0.4 mm media beads in a Netzsch Labstar laboratory scale mill for 4 hours to a target particle size of 150 nm. The sample was diluted to 16% solids. The obtained dispersion was filtered with a 0.5 micron filter.

Example 3 dispersion ("Ex. 3"): In a stainless steel vessel, dry Pigment Red 122 (300 g, Ink Jet Magenta E 02, Clariant) and 33 g of synergist (V)+(VI) mixture were combined with 1000 g water and 7 g of sodium carbonate. The mixture was homogenized with an overhead rotor-stator high shear mixer (Silverson L4RT-A) for 10 minutes at 5,000 rpm. The mixture was then milled with 0.4 mm media beads in a Netzsch Labstar laboratory scale mill for 2 hours to a target particle size of 150 nm. The sample was diluted to 16% solids. Excess salts were removed with one volume of ultrafiltration by using a GE Healthcare hollow fiber cartridge membrane filter (0.1 micron pore size). The obtained dispersion was filtered with a 0.5 micron filter.

The dispersions C1 and Ex. 1-3 were aged for 1 week at 60° C.; properties are listed in Table 1.

TABLE 1

| Dispersion | Quinacridone | Solids % | pH | Initial Median particle size, nm | Median particle size, 1 week at 60° C. |
|---|---|---|---|---|---|
| C1 | (IV) | 13.8% | 9.0 | 158 nm | gelled (24 hours) |
| Ex. 1 | (V + VI) | 13.5% | 8.4 | 162 nm | 159 nm |
| Ex. 2 | (V + VI) | 15.41% | 7.7 | 159 nm | 158 nm |
| Ex. 3 | (V + VI) | 16.69% | 7.15 | 161 nm | 157 nm |

The exemplified quinacridone synergists differed from the comparative quinacridone by the incorporation of an additional methylene group binding the carboxyl to the quinacridone ring system. From Table 1, it can be seen that the pigment dispersions comprising the quinacridone synergists exemplifying the claimed invention substantially maintained the median particle size after one week, whereas the comparative dispersion gelled after 24 h. This indicates that the claimed synergists imparted greater stability to the quinacridone pigment dispersions compared to the comparative quinacridone dispersions.

The use of the terms "a" and "an" and "the" are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. A composition comprising at least one quinacridone magenta pigment and at least one synergist selected from compounds (A) and (B) having the following structures:

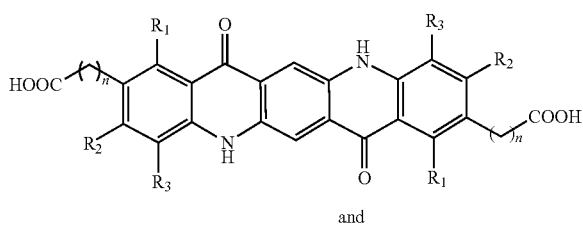

and

-continued

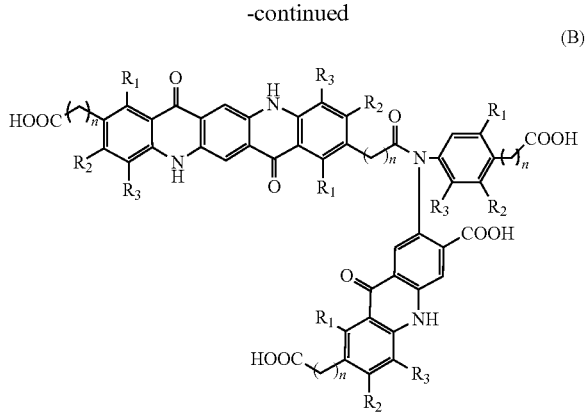

wherein each n is an integer independently ranging from 1 to 4, and $R_1$-$R_3$ are each independently selected from H, $CH_3$, Cl, and F.

2. The composition of claim 1, wherein the at least one quinacridone magenta pigment is selected from Pigment Violet 19, Pigment Red 122, Pigment Red 192, Pigment Red 202, Pigment Red 207, Pigment Red 209, and Pigment Red 282.

3. The composition of claim 1, wherein the at least one synergist is present in the composition in an amount ranging from 3% to 10% by weight relative to the weight of the at least one quinacridone magenta pigment.

4. The composition of claim 1, wherein the at least one synergist comprises compounds having structure (A) and structure (B).

5. The composition of claim 4, wherein the compounds of structure (A) and (B) are present in an (A):(B) ratio ranging from 1:10 to 10:1.

6. The composition of claim 1, wherein the at least one synergist is selected from compounds having structure (A) only.

7. The composition of claim 1, wherein the at least one synergist is selected from compounds having structure (B) only.

8. The composition of claim 1, wherein $R_1$-$R_3$ are each independently selected from H, $CH_3$, and Cl.

9. The composition of claim 1, wherein $R_1$-$R_3$ are H.

10. The composition of claim 1, wherein each n is an integer independently selected from 1 or 2.

11. The composition of claim 1, wherein each n is 1.

12. The composition of claim 1, wherein the at least one quinacridone pigment has a median particle size ranging from 100 nm to 300 nm.

13. The composition of claim 1, wherein the at least one quinacridone pigment has a median particle size ranging from 100 nm to 200 nm.

14. The composition of claim 1, wherein the composition further comprises a liquid vehicle.

15. The composition of claim 14, wherein the liquid vehicle comprises water.

16. The composition of claim 15, wherein the liquid vehicle further comprises at least one solvent.

17. The composition of claim 1, wherein the composition is an aqueous pigment dispersion.

18. The composition of claim 1, wherein the composition is an aqueous ink composition.

\* \* \* \* \*